(12) United States Patent
Lim (10) Patent No.: US 12,258,396 B1
(45) Date of Patent: Mar. 25, 2025

(54) METHODS OF USING IMMUNOTHERAPEUTICS THAT BIND FOLATE RECEPTOR ALPHA

(71) Applicant: Medicovestor, Inc., Wilmington, DE (US)

(72) Inventor: Seah Lim, Wilmington, DE (US)

(73) Assignee: MEDICOVESTOR, INC., Wilmington, DE (US)

( * ) Notice: Subject to any disclaimer, the term of this patent is extended or adjusted under 35 U.S.C. 154(b) by 0 days.

(21) Appl. No.: 18/431,767

(22) Filed: Feb. 2, 2024

(51) Int. Cl.
*C07K 16/28* (2006.01)
*G01N 33/574* (2006.01)

(52) U.S. Cl.
CPC ........... *C07K 16/28* (2013.01); *G01N 33/574* (2013.01); *C07K 2317/565* (2013.01); *C07K 2317/73* (2013.01); *G01N 2333/705* (2013.01)

(58) Field of Classification Search
None
See application file for complete search history.

(56) References Cited

U.S. PATENT DOCUMENTS

| | | | |
|---|---|---|---|
| 5,731,168 A | 3/1998 | Carter et al. | |
| 5,877,296 A | 3/1999 | Hamann et al. | |
| 6,565,827 B1 | 5/2003 | Kaminski et al. | |
| 7,422,739 B2 | 9/2008 | Anderson et al. | |
| 7,446,190 B2 | 11/2008 | Sadelain et al. | |
| 7,741,465 B1 | 6/2010 | Eshhar et al. | |
| 8,088,387 B2 | 1/2012 | Steeves et al. | |
| 8,277,806 B2 | 10/2012 | Lindhofer | |
| 8,592,562 B2 | 11/2013 | Kannan et al. | |
| 9,499,629 B2 | 11/2016 | June et al. | |
| 9,505,848 B2 | 11/2016 | Davis et al. | |
| 9,695,237 B2 * | 7/2017 | Ando | C12N 15/09 |
| 9,862,769 B2 | 1/2018 | De Goeij et al. | |
| 10,011,858 B2 | 7/2018 | Igawa et al. | |
| 10,322,192 B2 | 6/2019 | Albone et al. | |
| 10,344,050 B2 | 7/2019 | Gramer et al. | |
| 10,517,960 B2 | 12/2019 | Jakobsen et al. | |
| 10,596,270 B2 | 3/2020 | Guillemont et al. | |
| 10,597,464 B2 | 3/2020 | Labrijn et al. | |
| 10,752,683 B2 | 8/2020 | Ab et al. | |
| 11,135,305 B2 * | 10/2021 | Carrigan | A61K 47/6851 |
| 11,597,766 B2 | 3/2023 | Zugmaier et al. | |
| 2023/0201210 A1 | 6/2023 | Sliwkowski et al. | |

OTHER PUBLICATIONS

Cheung et al., Targeting folate receptor alpha for cancer treatment. Oncotarget 7 (32): 52553-52574, May 27, 2016.*
Scaranti et al., Exploiting the folate receptor a in oncology. Nature Reviews Clinical Oncology 17:349-359, 2020.*
Shopes, B., A genetically engineered human IgG mutant with enhanced cytolytic activity, The Journal of Immunology, May 1, 1992, 148(9):2918- 22.
Shopes, B., A genetically engineered human IgG with limited flexibility fully initiates cytolysis via complement, Molecular Immunology, Apr. 1993, 30(6):603-9.
Van Der Neut Kolfschoten, M. et al., Anti-inflammatory activity of human IgG4 antibodies by dynamic Fab arm exchange, Science, Sep. 14, 2007, 317(5844):1554-7.

* cited by examiner

*Primary Examiner* — Ruixiang Li
(74) *Attorney, Agent, or Firm* — HOLLAND & HART LLP (57) ABSTRACT

This disclosure describes methods of using proteins that specifically bind human folate receptor alpha (FRalpha) with high affinity. These proteins include a recombinant human anti-FRalpha IgG1 that is suitable for use as a therapeutic antibody to treat cancers that express FRalpha. Other FRalpha-binding proteins are also described including antibody fragments, antibody conjugates, and fusion proteins.

9 Claims, 3 Drawing Sheets
Specification includes a Sequence Listing.

SEQUENCE LISTING

```
Sequence total quantity: 12
SEQ ID NO: 1            moltype = DNA  length = 354
FEATURE                 Location/Qualifiers
source                  1..354
                        mol_type = other DNA
                        organism = Synthetic construct
SEQUENCE: 1
gaggtgcagc tgttggagtc tgggggaggc ttggtcaagc ctggggggtc cctgagactc   60
tcctgtgcag cctctggatt caccttcagt agctatacca tgaactgggt ccgccaggct  120
ccagggaagg ggctggaatg ggtctcatcc attagtagtg gtggtggtta catatactac  180
gcagactcag tgaaggaccg attcaccatc tccagagaca acgccaagaa ctcactgtat  240
ctgcaaatga acagcctgcg agccgaggac acggccgtgt attactgtgc aaaaggggat  300
acgatcatga taatatcggc gtggggccaa gggacaacgg tcaccgtctc atca        354

SEQ ID NO: 2            moltype = DNA  length = 321
FEATURE                 Location/Qualifiers
source                  1..321
                        mol_type = other DNA
                        organism = Synthetic construct
SEQUENCE: 2
gacatccagt tgacccagtc tccttccacc ctgtctgcat ctgtaggaga cagagtcacc   60
atcacttgcc gggccagtca gagtattagt agttggttgg cctggcatca gcagaaacca  120
gggaaagccc ctaaactcct catctatgct gcatccagtt tgcaaaatgg ggtcccatca  180
aggttcagcg gcagtggatt tgggacagat ttcactctca ccatcagcag cctgcagcct  240
gaagactttg caacttacta ttgtcaacag gctagcagtt tccctctcac tttcggcgga  300
gggaccaagg tggagatcaa a                                            321

SEQ ID NO: 3            moltype = AA  length = 118
```

```
FEATURE                 Location/Qualifiers
source                  1..118
                        mol_type = protein
                        organism = Synthetic construct
SEQUENCE: 3
EVQLLESGGG LVKPGGSLRL SCAASGFTFS SYTMNWVRQA PGKGLEWVSS ISSGGGYIYY    60
ADSVKDRFTI SRDNAKNSLY LQMNSLRAED TAVYYCAKGD TIMIISAWGQ GTTVTVSS    118

SEQ ID NO: 4            moltype = AA   length = 107
FEATURE                 Location/Qualifiers
source                  1..107
                        mol_type = protein
                        organism = Synthetic construct
SEQUENCE: 4
DIQLTQSPST LSASVGDRVT ITCRASQSIS SWLAWHQQKP GKAPKLLIYA ASSLQNGVPS    60
RFSGSGFGTD FTLTISSLQP EDFATYYCQQ ASSFPLTFGG GTKVEIK                107

SEQ ID NO: 5            moltype = AA   length = 10
FEATURE                 Location/Qualifiers
source                  1..10
                        mol_type = protein
                        organism = Synthetic construct
SEQUENCE: 5
GFTFSSYTMN                                                           10

SEQ ID NO: 6            moltype = AA   length = 17
FEATURE                 Location/Qualifiers
source                  1..17
                        mol_type = protein
                        organism = Synthetic construct
SEQUENCE: 6
SISSGGGYIY YADSVKD                                                   17

SEQ ID NO: 7            moltype = AA   length = 11
FEATURE                 Location/Qualifiers
source                  1..11
                        mol_type = protein
                        organism = Synthetic construct
SEQUENCE: 7
AKGDTIMIIS A                                                         11

SEQ ID NO: 8            moltype = AA   length = 11
FEATURE                 Location/Qualifiers
source                  1..11
                        mol_type = protein
                        organism = Synthetic construct
SEQUENCE: 8
RASQSISSWL A                                                         11

SEQ ID NO: 9            moltype = AA   length = 7
FEATURE                 Location/Qualifiers
source                  1..7
                        mol_type = protein
                        organism = Synthetic construct
SEQUENCE: 9
AASSLQN                                                               7

SEQ ID NO: 10           moltype = AA   length = 10
FEATURE                 Location/Qualifiers
source                  1..10
                        mol_type = protein
                        organism = Synthetic construct
SEQUENCE: 10
QQASSFPLTF                                                           10

SEQ ID NO: 11           moltype = AA   length = 448
FEATURE                 Location/Qualifiers
source                  1..448
                        mol_type = protein
                        organism = Synthetic construct
SEQUENCE: 11
EVQLLESGGG LVKPGGSLRL SCAASGFTFS SYTMNWVRQA PGKGLEWVSS ISSGGGYIYY    60
ADSVKDRFTI SRDNAKNSLY LQMNSLRAED TAVYYCAKGD TIMIISAWGQ GTTVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448
```

```
SEQ ID NO: 12          moltype = AA  length = 214
FEATURE                Location/Qualifiers
source                 1..214
                       mol_type = protein
                       organism = Synthetic construct
SEQUENCE: 12
DIQLTQSPST LSASVGDRVT ITCRASQSIS SWLAWHQQKP GKAPKLLIYA ASSLQNGVPS   60
RFSGSGFGTD FTLTISSLQP EDFATYYCQQ ASSFPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

METHODS OF USING IMMUNOTHERAPEUTICS THAT BIND FOLATE RECEPTOR ALPHA

SEQUENCE LISTING

This disclosure includes a sequence listing, which has file name "sequence_listing_1200590017.xml," which was created on Feb. 2, 2024, which has a file size of 12,764 bytes, and which is incorporated by reference in its entirety.

FIELD OF THE INVENTION

The present invention relates to proteins that bind folate receptor alpha (FRalpha), which FRalpha-binding proteins are derived from an anti-FRalpha Fab and include anti-FRalpha monoclonal antibodies as well as FRalpha-binding conjugates and fusion proteins derived from the complementarity determining regions (CDRs) of the Fab. The present invention specifically relates to the use of FRalpha-binding proteins in the diagnosis and treatment of various health conditions including cancer.

BACKGROUND OF SOME ASPECTS OF THE SPECIFICATION

A number of different cancers overexpress FRalpha including ovarian, breast, renal, lung, colorectal, and brain cancers. A number of different monoclonal antibodies have therefore been developed to treat cancer by targeting FRalpha. An initial monoclonal antibody farletuzumab failed to meet its primary endpoint in phase III clinical trials in subjects with epithelial ovarian cancer and also failed in subjects with lung cancer. Bristol-Myers Squibb nevertheless subsequently paid $650 million to Eisai in 2021 to develop and commercialize a farletuzumab antibody-drug conjugate, farletuzumab ecteribulin, which also entitles Eisai to $2.45 billion for meeting future development, regulatory, and commercial milestones. The United States Food and Drug Administration (FDA) granted accelerated approval to first-in-class anti-FRalpha antibody-drug conjugate mirvetuximab soravtansine (ELAHERE®) in November, 2022, for treating FRalpha positive, platinum-resistant epithelial ovarian, fallopian tube, and primary peritoneal cancer, which supported the exit of its maker ImmunoGen to AbbVie at a valuation exceeding $10 billion the following year. Other FRalpha antibody-drug conjugates in development include luveltamab tazevibulin, which received fast track designation from the FDA in 2021. In sum, the tremendous promise of anti-FRalpha therapeutics to treat a range of prevalent cancers underpins tremendous value.

SUMMARY OF SOME ASPECTS OF THE SPECIFICATION

Various aspects of this disclosure relate to the discovery of a novel anti-FRalpha Fab that includes CDRs that have nanomolar affinity for FRalpha. The CDRs retain their affinity in IgG formats. A human antibody comprising the CDRs is in pre-clinical development for use as a cancer immunotherapeutic. The CDRs notably cross-react with cynomolgus FRalpha, which allows for pre-clinical trials in primates. The CDRs are also compatible with a full range of immunotherapeutic strategies including antibody conjugates, bi-specific proteins (for example, as T-cell engagers), and adoptive cell therapies (for example, as CAR-Ts). The CDRs may also be cloned into antibodies for laboratory research and diagnostics. The following disclosure describes, for example, a fully human IgG1, which is currently in pre-clinical development for use as a cancer immunotherapeutic.

The preceding Background and Summary sections are provided as a brief introduction to the described subject matter as well as a synopsis of some of the technological improvements and advantages that it provides. The Background and Summary shall not be construed as identifying essential aspects of the described subject matter, nor shall they be construed to limit the interpretation of this specification or any patent claim that matures from this specification.

BRIEF DESCRIPTION OF THE DRAWINGS

A further understanding of this specification may be appreciated with reference to the following drawings. The drawings are exemplary, and neither this specification nor any patent claim that matures from this specification shall be construed as limited by the drawings.

DETAILED DESCRIPTION

Various aspects of this disclosure relate to antibodies that display high-affinity for FRalpha. These antibodies were developed using a Fab phage-display bio-panning strategy on a library generated from the peripheral blood of 120 healthy donors as set forth in the Example below. The library included about a trillion different combinations. The best-performing Fab in the library had an immunoglobulin heavy chain variable region (VH) with the nucleotide sequence of SEQ ID NO: 1 and an immunoglobulin light chain variable region (VL) with the nucleotide sequence of SEQ ID NO: 2, which nucleotide sequences are depicted in Table 1 below. The VH amino acid sequence is of SEQ ID NO: 3, and the VL amino acid sequence is of SEQ ID NO: 4. The VH and VL amino acid sequences are depicted in Table 2 below, in which CDRs are depicted with bold and underline, and in which framework regions are depicted with plain text. CDR sequences are of SEQ ID NO: 5-10 and are independently depicted in Table 3 below. One of ordinary skill will recognize that the precise demarcation between CDR and framework regions is blurred at least for some of the CDRs, and the CDRs as set forth in Tables 2 and 3 and in SEQ ID NO: 5-10 may therefore include one or more amino acids that might be more-appropriately classified as framework rather than CDR.

Nucleotide sequences encoding the variable regions of the best-performing Fab (SEQ ID NO: 1 and 2) were cloned into a human IgG1 heavy chain gene and a human kappa light chain gene to express a fully-human monoclonal antibody. The full heavy chain has the amino acid sequence of SEQ ID NO: 10 and the full light chain has the amino acid sequence of SEQ ID NO: 11, which are depicted in Table 4 below. The affinity of the antibody for FRalpha was determined to be sub-nanomolar by ELISA and flow cytometry.

Various aspects of this disclosure relate to a kit, comprising a recombinant anti-FRalpha antibody as described anywhere in this disclosure and a reporter, wherein the kit is configured to detect FRalpha in a biological sample. In some embodiments, the reporter comprises either (i) a conjugated dye or (ii) a conjugated fluorescent, phosphorescent, chemiluminescent, radioactive, or magnetic label. In some specific embodiments, the reporter comprises a secondary antibody; the conjugated dye is an antibody-conjugated dye; and the conjugated fluorescent, phosphorescent, chemiluminescent, radioactive, or magnetic label is an antibody-conjugated fluorescent, phosphorescent, chemiluminescent, radioactive, or magnetic label. In some very specific embodiments, the kit is configured to detect FRalpha in the biological sample by immunohistochemistry, western blotting, flow cytometry, magnetic-activated cell sorting, ELISA, or chemiluminescent immunoassay.

Various aspects of this disclosure relate to a recombinant anti-FRalpha antibody or antigen-binding fragment thereof, which comprises the CDRs described herein or which comprises sequence homology (or sequence identity) with the VH and VL variable regions that comprise the CDRs described herein. In all embodiments, the antibody or antigen-binding fragment thereof binds human FRalpha.

The term "antibody" includes immunoglobulins (Ig's) of different classes (for example, IgA, IgG, IgM, IgD, and IgE) and subclasses (for example, IgG1, IgG2a, and IgG4) and also includes mouse antibodies, fully-human antibodies, chimeric human/animal antibodies, and engineered variants thereof. This specification describes, for example, a fully-human IgG1 antibody.

The term "antigen-binding fragment" refers to both Fab fragments and single-chain variable fragments (ScFv). scFvs are fusion proteins of two variable regions connected with a flexible linker, which fusion proteins retain antigen-binding properties comparable to a Fab. Examples of scFvs include brolucizumab (also known as BEOVU®).

As used in this disclosure, the term "sequence homology" refers to percent "positives" as determined by Standard Protein BLAST® over the full length of a sequence set forth in a SEQ ID NO. Standard Protein BLAST® is available at https://blast.ncbi.nlm.nih.gov/Blast.cgi?PROGRAM=blastp. BLAST® is generally described in Altschul, et al. (1997), "Gapped BLAST and PSI-BLAST: a new generation of protein database search programs", Nucleic Acids Res. 25:3389-3402, and in Altschul, et al. (2005) "Protein database searches using compositionally adjusted substitution matrices", FEBS J. 272: 5101-5109. As used in this disclosure, the term "sequence identity" refers to the percent of exact matches over the full length of a sequence set forth in a SEQ ID NO.

In all embodiments, the recombinant anti-FRalpha antibody or antigen-binding fragment thereof comprises two variable domains. The two variable domains include a heavy chain variable region and a light chain variable region. In some specific embodiments, the heavy chain variable region has a percent sequence homology (or sequence identity) with SEQ ID NO: 5, 6, and 7, and the light chain variable region has a percent sequence homology (or sequence identity) with SEQ ID NO: 8, 9, and 10. In some very specific embodiments, the heavy chain variable region has a percent sequence homology (or sequence identity) with SEQ ID NO: 3, and the light chain variable region has a percent sequence homology (or sequence identity) with SEQ ID NO: 4.

In some embodiments, the antibody or antigen-binding fragment thereof comprises (1) a first variable domain that comprises a VH CDR1 region comprising an amino acid sequence that is identical to at least 7, 8, 9, or 10 consecutive amino acids of SEQ ID NO: 5, a VH CDR2 region comprising an amino acid sequence that is identical to at least 7, 8, 9, 10, 11, 12, 13, 14, 15, 16, or 17 consecutive amino acids of SEQ ID NO: 6, and a VH CDR3 region comprising an amino acid sequence that is identical to at least 7, 8, 9, 10, or 11 consecutive amino acids of SEQ ID NO: 7; and (2) a second variable domain that comprises a VL CDR1 region comprising an amino acid sequence that is identical to at least 7, 8, 9, 10, or 11 consecutive amino acids of SEQ ID NO: 8, a VL CDR2 region comprising an amino acid sequence that is identical to at least 3, 4, 5, 6, or 7 consecutive amino acids of SEQ ID NO: 9, and a VL CDR3 region comprising an amino acid sequence that is identical to at least 3, 4, 5, 6, 7, 8, 9, or 10 consecutive amino acids of SEQ ID NO: 10.

In some embodiments, the recombinant anti-FRalpha antibody comprises four variable domains, wherein the antibody comprises (1) a third variable domain that comprises a VH CDR1 region comprising an amino acid sequence that is identical to at least 7, 8, 9, or 10 consecutive amino acids of SEQ ID NO: 5, a VH CDR2 region comprising an amino acid sequence that is identical to at least 7, 8, 9, 10, 11, 12, 13, 14, 15, 16, or 17 consecutive amino acids of SEQ ID NO: 6, and a VH CDR3 region comprising an amino acid sequence that is identical to at least 7, 8, 9, 10, or 11 consecutive amino acids of SEQ ID NO: 7; and (2) a fourth variable domain that comprises a VL CDR1 region comprising an amino acid sequence that is identical to at least 7, 8, 9, 10, or 11 consecutive amino acids of SEQ ID NO: 8, a VL CDR2 region comprising an amino acid sequence that is identical to at least 3, 4, 5, 6, or 7 consecutive amino acids of SEQ ID NO: 9, and a VL CDR3 region comprising an amino acid sequence that is identical to at least 3, 4, 5, 6, 7, 8, 9, or 10 consecutive amino acids of SEQ ID NO: 10. Such antibodies include, for example, IgG antibodies.

In some embodiments, one or more of VH CDR1, VH CDR2, VH CDR3, VL CDR1, VL CDR2, and VL CDR3 comprise one or more conservative mutations. Conservative mutations are known in the art and include, for example, threonine to serine, isoleucine to valine or leucine, tyrosine to phenylalanine, aspartate to glutamate, asparagine to glutamine, arginine to lysine, and like substitutions. In this disclosure, a conservative mutation is a "positive" match in Standard Protein BLAST® that is not an identity.

Various aspects of this disclosure relate to a recombinant anti-FRalpha antibody or antigen-binding fragment thereof, comprising two variable domains, wherein: the antibody or antigen-binding fragment thereof comprises a first variable domain that comprises an amino acid sequence that has at least 90 percent sequence homology with SEQ ID NO: 3; the antibody or antigen-binding fragment thereof comprises a second variable domain that comprises an amino acid sequence that has at least 90 percent sequence homology with SEQ ID NO: 4; and the antibody or antigen-binding fragment thereof binds human FRalpha. In some specific embodiments, the first variable domain comprises an amino acid sequence that has at least 90 percent sequence identity with SEQ ID NO: 3; the second variable domain comprises an amino acid sequence that has at least 90 percent sequence identity with SEQ ID NO: 4; and the antibody or antigen-binding fragment thereof binds human FRalpha.

SEQ ID NO: 3 is a VH amino acid sequence, which includes VH CDR1, VH CDR2, VH CDR3, and framework regions. In some embodiments, the VH amino acid sequence comprises mutations relative to SEQ ID NO: 3 such that the VH amino acid sequence has at least 90 percent sequence homology with SEQ ID NO: 3 but less than 100 percent sequence homology. In some specific embodiments, the VH amino acid sequence comprises mutations relative to SEQ ID NO: 3 such that the VH amino acid sequence has at least 90 percent sequence identity with SEQ ID NO: 3 but less than 100 percent sequence identity.

SEQ ID NO: 4 is a VL amino acid sequence, which includes VL CDR1, VL CDR2, VL CDR3, and framework regions. In some embodiments, the VL amino acid sequence comprises mutations relative to SEQ ID NO: 4 such that the VL amino acid sequence has at least 90 percent sequence homology with SEQ ID NO: 4 but less than 100 percent sequence homology. In some specific embodiments, the VL amino acid sequence comprises mutations relative to SEQ ID NO: 4 such that the VL amino acid sequence has at least 90 percent sequence identity with SEQ ID NO: 4 but less than 100 percent sequence identity.

Mutations to the VH and/or VL amino acid sequences may be engineered, for example, to tune the avidity of an antibody (or antigen-binding fragment thereof) to the FRalpha antigen, to modulate expression or glycosylation, and/or for other purposes.

In some embodiments, the first variable domain comprises an amino acid sequence that has at least 95 percent sequence homology with SEQ ID NO: 3. In some specific embodiments, the first variable domain comprises an amino acid sequence that has at least 97 percent sequence homology with SEQ ID NO: 3. In some even more specific embodiments, the first variable domain comprises an amino acid sequence that has at least 98 percent sequence homology with SEQ ID NO: 3. In some very specific embodiments, the first variable domain comprises an amino acid sequence that has at least 99 percent sequence homology with SEQ ID NO: 3.

In some embodiments, the first variable domain comprises an amino acid sequence that has at least 95 percent sequence identity with SEQ ID NO: 3. In some specific embodiments, the first variable domain comprises an amino acid sequence that has at least 97 percent sequence identity with SEQ ID NO: 3. In some even more specific embodiments, the first variable domain comprises an amino acid sequence that has at least 98 percent sequence identity with SEQ ID NO: 3. In some very specific embodiments, the first variable domain comprises an amino acid sequence that has at least 99 percent sequence identity with SEQ ID NO: 3.

In some embodiments, the second variable domain comprises an amino acid sequence that has at least 95 percent sequence homology with SEQ ID NO: 4. In some specific embodiments, the second variable domain comprises an amino acid sequence that has at least 97 percent sequence homology with SEQ ID NO: 4. In some even more specific embodiments, the second variable domain comprises an amino acid sequence that has at least 98 percent sequence homology with SEQ ID NO: 4. In some very specific embodiments, the second variable domain comprises an amino acid sequence that has at least 99 percent sequence homology with SEQ ID NO: 4.

In some embodiments, the second variable domain comprises an amino acid sequence that has at least 95 percent sequence identity with SEQ ID NO: 4. In some specific embodiments, the second variable domain comprises an amino acid sequence that has at least 97 percent sequence identity with SEQ ID NO: 4. In some even more specific embodiments, the second variable domain comprises an amino acid sequence that has at least 98 percent sequence identity with SEQ ID NO: 4. In some very specific embodiments, the second variable domain comprises an amino acid sequence that has at least 99 percent sequence identity with SEQ ID NO: 4.

In some embodiments, the recombinant anti-FRalpha antibody comprises four variable domains, wherein the antibody comprises (1) a third variable domain that comprises an amino acid sequence that has at least 90 percent sequence homology with SEQ ID NO: 3 (such as at least 95, 97, 98, or 99 percent sequence homology); and (2) a fourth variable domain that comprises an amino acid sequence that has at least 90 percent sequence homology with SEQ ID NO: 4 (such as at least 95, 97, 98, or 99 percent sequence homology). In some specific embodiments, the third variable domain comprises an amino acid sequence that has at least 90 percent sequence identity with SEQ ID NO: 3 (such as at least 95, 97, 98, or 99 percent sequence homology), and the fourth variable domain comprises an amino acid sequence that has at least 90 percent sequence identity with SEQ ID NO: 4 (such as at least 95, 97, 98, or 99 percent sequence identity).

In some embodiments, the recombinant anti-FRalpha antibody or antigen-binding fragment thereof has a KD with human FRalpha of no greater than 50 nanomolar. In some specific embodiments, the recombinant anti-FRalpha antibody or antigen-binding fragment thereof has a KD with human FRalpha of no greater than 25 nanomolar. In some very specific embodiments, the recombinant anti-FRalpha antibody or antigen-binding fragment thereof has a KD with human FRalpha of no greater than 10 nanomolar.

In some embodiments, KD is determined by ELISA.

In some embodiments, the recombinant anti-FRalpha antibody comprises an IgG heavy chain constant region. In some specific embodiments, the recombinant anti-FRalpha antibody comprises an IgG1 heavy chain constant region. In some specific embodiments, the recombinant anti-FRalpha antibody comprises an IgG4 heavy chain constant region.

In some embodiments, the recombinant anti-FRalpha antibody comprises a kappa or lambda light chain constant region. In some specific embodiments, the recombinant anti-FRalpha antibody comprises a kappa light chain constant region.

In some embodiments, the recombinant anti-FRalpha antibody comprises a human heavy chain constant region and a human light chain constant region. In some specific embodiments, the recombinant anti-FRalpha antibody comprises a human IgG heavy chain constant region and a human kappa or lambda light chain constant region. In some very specific embodiments, the recombinant anti-FRalpha antibody comprises a human IgG1 heavy chain constant region and a human kappa light chain constant region.

In some embodiments, the recombinant anti-FRalpha antibody has a heavy chain that has at least 90 percent sequence homology with SEQ ID NO: 11. In some specific embodiments, the recombinant anti-FRalpha antibody has a heavy chain that has at least 95 percent sequence homology with SEQ ID NO: 11. In some even more specific embodiments, the recombinant anti-FRalpha antibody has a heavy chain that has at least 98 percent sequence homology with SEQ ID NO: 11. In some very specific embodiments, the recombinant anti-FRalpha antibody has a heavy chain that has at least 99 percent sequence homology with SEQ ID NO: 11.

In some embodiments, the recombinant anti-FRalpha antibody has a heavy chain that has at least 90 percent sequence identity with SEQ ID NO: 11. In some specific embodiments, the recombinant anti-FRalpha antibody has a heavy chain that has at least 95 percent sequence identity with SEQ ID NO: 11. In some even more specific embodiments, the recombinant anti-FRalpha antibody has a heavy chain that has at least 98 percent sequence identity with SEQ ID NO: 11. In some very specific embodiments, the recombinant anti-FRalpha antibody has a heavy chain that has at least 99 percent sequence identity with SEQ ID NO: 11.

In some embodiments, the recombinant anti-FRalpha antibody has a light chain that has at least 90 percent sequence homology with SEQ ID NO: 12. In some specific embodiments, the recombinant anti-FRalpha antibody has a light chain that has at least 95 percent sequence homology with SEQ ID NO: 12. In some even more specific embodiments, the recombinant anti-FRalpha antibody has a light chain that has at least 98 percent sequence homology with SEQ ID NO: 12. In some very specific embodiments, the recombinant anti-FRalpha antibody has a light chain that has at least 99 percent sequence homology with SEQ ID NO: 12.

In some embodiments, the recombinant anti-FRalpha antibody has a light chain that has at least 90 percent sequence identity with SEQ ID NO: 12. In some specific embodiments, the recombinant anti-FRalpha antibody has a light chain that has at least 95 percent sequence identity with SEQ ID NO: 12. In some even more specific embodiments, the recombinant anti-FRalpha antibody has a light chain that has at least 98 percent sequence identity with SEQ ID NO: 12. In some very specific embodiments, the recombinant anti-FRalpha antibody has a light chain that has at least 99 percent sequence identity with SEQ ID NO: 12.

In some embodiments, the recombinant anti-FRalpha antibody has (1) a heavy chain that has at least 90 percent sequence homology with SEQ ID NO: 11, and (2) a light chain that has at least 90 percent sequence homology with SEQ ID NO: 12. In some specific embodiments, the recombinant anti-FRalpha antibody has (1) a heavy chain that has at least 95 percent sequence homology with SEQ ID NO: 11, and (2) a light chain that has at least 95 percent sequence homology with SEQ ID NO: 12. In some even more specific embodiments, the recombinant anti-FRalpha antibody has (1) a heavy chain that has at least 98 percent sequence homology with SEQ ID NO: 11, and (2) a light chain that has at least 98 percent sequence homology with SEQ ID NO: 12. In some very specific embodiments, the recombinant anti-FRalpha antibody has (1) a heavy chain that has at least 99 percent sequence homology with SEQ ID NO: 11, and (2) a light chain that has at least 99 percent sequence homology with SEQ ID NO: 12.

In some embodiments, the recombinant anti-FRalpha antibody has (1) a heavy chain that has at least 90 percent sequence identity with SEQ ID NO: 11, and (2) a light chain that has at least 90 percent sequence identity with SEQ ID NO: 12. In some specific embodiments, the recombinant anti-FRalpha antibody has (1) a heavy chain that has at least 95 percent sequence identity with SEQ ID NO: 11, and (2) a light chain that has at least 95 percent sequence identity with SEQ ID NO: 12. In some even more specific embodiments, the recombinant anti-FRalpha antibody has (1) a heavy chain that has at least 98 percent sequence identity with SEQ ID NO: 11, and (2) a light chain that has at least 98 percent sequence identity with SEQ ID NO: 12. In some very specific embodiments, the recombinant anti-FRalpha antibody has (1) a heavy chain that has at least 99 percent sequence identity with SEQ ID NO: 11, and (2) a light chain that has at least 99 percent sequence identity with SEQ ID NO: 12.

In some embodiments, the recombinant anti-FRalpha antibody comprises two heavy chains and two light chains, wherein each of the two heavy chains has at least 90 percent sequence homology with SEQ ID NO: 11, and each of the two light chains has at least 90 percent sequence homology with SEQ ID NO: 12. In some specific embodiments, the recombinant anti-FRalpha antibody comprises two heavy chains and two light chains, wherein each of the two heavy chains has at least 95 percent sequence homology with SEQ ID NO: 11, and each of the two light chains has at least 95 percent sequence homology with SEQ ID NO: 12. In some even more specific embodiments, the recombinant anti-FRalpha antibody comprises two heavy chains and two light chains, wherein each of the two heavy chains has at least 98 percent sequence homology with SEQ ID NO: 11, and each of the two light chains has at least 98 percent sequence homology with SEQ ID NO: 12. In some very specific embodiments, the recombinant anti-FRalpha antibody comprises two heavy chains and two light chains, wherein each of the two heavy chains has at least 99 percent sequence homology with SEQ ID NO: 11, and each of the two light chains has at least 99 percent sequence homology with SEQ ID NO: 12. Such antibodies include, for example, IgG1 antibodies.

In some embodiments, the recombinant anti-FRalpha antibody comprises two heavy chains and two light chains, wherein each of the two heavy chains has at least 90 percent sequence identity with SEQ ID NO: 11, and each of the two light chains has at least 90 percent sequence identity with SEQ ID NO: 12. In some specific embodiments, the recombinant anti-FRalpha antibody comprises two heavy chains and two light chains, wherein each of the two heavy chains has at least 95 percent sequence identity with SEQ ID NO: 11, and each of the two light chains has at least 95 percent sequence identity with SEQ ID NO: 12. In some even more specific embodiments, the recombinant anti-FRalpha antibody comprises two heavy chains and two light chains, wherein each of the two heavy chains has at least 98 percent sequence identity with SEQ ID NO: 11, and each of the two light chains has at least 98 percent sequence identity with SEQ ID NO: 12. In some very specific embodiments, the recombinant anti-FRalpha antibody comprises two heavy chains and two light chains, wherein each of the two heavy chains has at least 99 percent sequence identity with SEQ ID NO: 11, and each of the two light chains has at least 99 percent sequence identity with SEQ ID NO: 12. Such antibodies include, for example, IgG1 antibodies.

In some embodiments, the recombinant anti-FRalpha antibody comprises at least four variable domains, wherein: the first and second variable domains are paired in the antibody such that the first and second variable domains bind an epitope of human FRalpha, and the antibody comprises a third variable domain and a fourth variable domain that are paired in the antibody such that the third and fourth variable domains bind a different epitope. Such antibodies include, for example, IgG-like bispecific antibodies such as trifunctional antibodies. The different epitope may be, for example, a CD3 epitope, and the antibody may function as a therapeutic antibody by crosslinking a cancer cell that expresses FRalpha with a T-cell that expresses CD3 and a leukocyte that expresses an Fc receptor (such as a monocyte, macrophage, natural killer cell, or dendritic cell), which binds to an Fc region of the antibody. Examples of trivalent antibodies include catumaxomab (also known as REMOVAB®), which binds the EpCAM cancer antigen, CD3, and Fc receptor (see, for example, U.S. Pat. No. 8,277,806, which is incorporated by reference in its entirety). Those of ordinary skill are capable of designing trivalent antibodies that bind FRalpha, CD3, and Fc receptor, for example, by replacing the catumaxomab variable regions that bind EpCAM with the variable regions set forth in SEQ ID NOs: 3 and 4. Other trivalent antibodies that bind FRalpha can be similarly engineered based on SEQ ID NOs: 3 and 4 and the known sequences of other existing trivalent antibodies. In some specific embodiments, the recombinant anti-FRalpha antibody comprises an Fc region. In some specific embodiments, the different epitope is an extracellular epitope of CD3. In some very specific embodiments, the recombinant anti-FRalpha antibody comprises an Fc region, and the different epitope is an extracellular epitope of CD3.

In this disclosure, the term "paired" refers a spatial proximity and orientation between VH and VL regions that allow the VH and VL regions to simultaneously bind an epitope. VH and VL regions may be paired, for example, in a Fab by quaternary structure that includes one or more disulfide bonds and non-covalent interactions between the heavy chain constant domain CHI and the light chain constant domain CL. VH and VL regions may also be paired, for example, as a scFv fusion protein, which generally includes a flexible linker, such as polyglycine, that tethers the VH and VL regions in spatial proximity and permits spatial orientations in which the VH and VL regions can simultaneously bind an epitope.

Various aspects of this disclosure relate to an antibody conjugate comprising a recombinant anti-FRalpha antibody as described anywhere in this disclosure, wherein the recombinant anti-FRalpha antibody is conjugated to a radioactive isotope or a pharmaceutical agent.

In some embodiments, the recombinant anti-FRalpha antibody is conjugated to a radioactive isotope. In some specific embodiments, the recombinant anti-FRalpha antibody is conjugated to a radioactive isotope selected from actinium-225, astatine-211, bismuth-212, bismuth-213, copper-67, gallium-68, holmium-166, iodine-124, iodine-131, lutetium-177, samarium-153, technetium-99, terbium-149, and yttrium-90. Examples of antibodies conjugated to radioactive isotopes include tositumomab (also known as BEXXAR®) and ibritumomab tiuxetan (also known as ZEVALIN®). Those of ordinary skill are capable of designing antibodies that are conjugated to radioactive isotopes using known strategies such as those used to conjugate iodine-131 in tositumomab and to conjugate yittrium-90 or indium-111 to ibritumomab (see, for example, U.S. Pat. Nos. 6,565,827 and 7,422,739, which are incorporated by reference in their entirety).

In some embodiments, the recombinant anti-FRalpha antibody is conjugated to a pharmaceutical agent. In some specific embodiments, the recombinant anti-FRalpha antibody is conjugated to a moiety selected from amanitin, 3-aminophenyl hemiasterlin, calicheamicin, camptothecin, deruxtecan, doxorubicin, emtansine, eribulin, exatecan, irinotecan, maleimidocaproyl monomethyl auristatin F, maytansine, mertansine (N2'-deacetyl-N2'-(3-mercapto-1-oxopropyl)-maytansine; DM1), monomethyl auristatin F, paclitaxel, PE38, pyrrolobenzodiazepine, ravtansine (N2'-deacetyl-N2'-(4-mercapto-4-methyl-1-oxopentyl) maytansine; DM4), SN-38, and vedotin. Examples of antibodies conjugated to pharmaceutical agents include gemtuzumab ozogamicin (also known as MYLOTARG®) and trastuzumab emtansine (also known as KADCYLA®). Those of ordinary skill are capable of designing antibodies that are conjugated to pharmaceutical agents using known strategies such as those used to conjugate calicheamicin to gemtuzumab and emtansine to trastuzumab (see, for example, U.S. Pat. Nos. 5,877,296 and 8,088,387, which are incorporated by reference in their entirety). Examples of anti-FRalpha immunoconjugates include farletuzumab ecteribulin, luveltamab tazevibulin, and mirvetuximab soravtansine (also known as ELAHERE®), which are described, for example, in U.S. Pat. Nos. 10,322,192, 10,596,270, 10,752,683, which are incorporated by reference in their entirety.

Various aspects of this disclosure relate to a pharmaceutical composition comprising a recombinant anti-FRalpha antibody, an antigen-binding fragment thereof, or a conjugate thereof as described anywhere in this disclosure and a pharmaceutically acceptable carrier. Suitable pharmaceutically acceptable carriers generally include water with dissolved solutes that buffer pH and provide metal cations and an ionic strength that stabilize an antibody or other therapeutic of this disclosure. Such formulations are generally sterile, and the selection and preparation of such pharmaceutically acceptable carriers are well known. Solid formats including lyophilized therapeutics generally include, for example, metal cations, anions, and optionally polyols such as sugars (for example, trehalose or glucose) that stabilize the therapeutic in the solid phase and during its reconstitution into an aqueous format. General guidance on selecting pharmaceutically acceptable carriers is available, for example, in REMINGTON: THE SCIENCE AND PRACTICE OF PHARMACY, 22nd edition (Allen Jr, Loyd V., editor) Pharmaceutical Press, 2012, and the skilled practitioner will also look to the formulations of the therapeutics described in this disclosure as well as other existing therapeutics in selecting a pharmaceutically acceptable carrier. Such guidance is generally available in the scientific literature and on existing product labels.

In some embodiments, the pharmaceutical composition is suitable for administration to a subject. In some specific embodiments, the pharmaceutical composition is suitable for administration to a human patient. In some very specific embodiments, the pharmaceutical composition is suitable for intravenous administration to a human patient.

In some embodiments, the pharmaceutical composition comprises an anti-FRalpha antibody, and the antibody has a purity of at least 85 percent relative to total protein in the pharmaceutical composition. In some specific embodiments, the pharmaceutical composition comprises an anti-FRalpha antibody, and the antibody has a purity of at least 90 percent relative to total protein in the pharmaceutical composition. In some very specific embodiments, the pharmaceutical composition comprises an anti-FRalpha antibody, and the antibody has a purity of at least 95 percent relative to total protein in the pharmaceutical composition.

In some embodiments, purity is determined by chromatography. In some specific embodiments, purity is determined by high-performance liquid chromatography (HPLC).

Various aspects of this disclosure relate to a kit, comprising (1) a hermetically-sealed container that contains a pharmaceutical composition as described anywhere in this specification and (2) instructions for use of the pharmaceutical composition.

Various aspects of this disclosure relate to a medical device, comprising the pharmaceutical composition as described anywhere in this specification. In some embodiments, the medical device is a syringe, a venous cannula, or a drug-eluting implant.

Various aspects of this disclosure relate to a method of treating or preventing cancer in a subject, comprising identifying that the subject comprises cells that express FRalpha and administering a pharmaceutical composition as described anywhere in this disclosure. Determining that the subject comprises cells that express FRalpha include, for example, identifying mRNA that encodes FRalpha by real-time reverse transcription-polymerase chain reaction (RT-PCR) and identifying FRalpha protein expression by flow cytometry and/or immunohistochemistry. Such methods may advantageously allow determination that a cancer cell expresses FRalpha, for example, based upon the prior selection of one or more cancer cells for analysis.

Various aspects of this disclosure relate to a method of treating or preventing cancer in a subject, comprising identifying that the subject comprises cells that express FRalpha above a certain threshold and administering a pharmaceutical composition as described anywhere in this disclosure. Determining that the subject comprises cells that express FRalpha above a certain threshold include, for example, identifying mRNA that encodes FRalpha by RT-PCR and identifying FRalpha protein expression by flow cytometry and/or immunohistochemistry. Such methods may advantageously allow determination that a cancer cell expresses FRalpha above a certain threshold, for example, based upon the prior selection of one or more cancer cells for analysis.

Various aspects of this disclosure relate to a method to modulate cells that express FRalpha in a human subject, comprising administering the immunotherapeutic agent to the human subject, wherein the immunotherapeutic agent is or comprises a recombinant anti-FRalpha antibody or antigen-binding fragment thereof as described anywhere in this disclosure. In some embodiments, the method is a method of treating or preventing cancer in a human subject. In some specific embodiments, the method is a method of treating or preventing cancer in a human subject, the human subject presents with cancer, and at least a portion of the cells that express FRalpha are cancer cells.

In some embodiments the immunotherapeutic agent is administered at an effective amount that is effective to induce cell death in at least a portion of the cells that express FRalpha, and the method modulates the cells that express FRalpha by inducing cell death. In some specific embodiments, the immunotherapeutic agent comprises an Fc region, and the method induces cell death by Fc receptor mediated binding and activation of one or more leukocytes to the cells that express FRalpha. In some specific embodiments, the immunotherapeutic agent is conjugated to a radioactive isotope, and the method induces cell death by emitting radiation within or in proximity to the cells that express FRalpha. In some specific embodiments, the immunotherapeutic agent is conjugated to a pharmaceutical agent, the pharmaceutical agent is cytotoxic, and the method induces cell death by releasing the pharmaceutical agent within or in proximity to the cells that express FRalpha. In some very specific embodiments, the immunotherapeutic agent is conjugated to a pharmaceutical agent by a labile linker, the pharmaceutical agent is cytotoxic, and the method induces cell death by releasing the pharmaceutical agent within or in proximity to the cells that express FRalpha.

In some embodiments, the subject is a mammal. In some specific embodiments, the subject is a rodent, lagomorph, feline, canine, porcine, ovine, caprine, *lama*, bovine, equine, or primate. In some very specific embodiments, the subject is a human patient.

In some embodiments, the subject is male or female. In some specific embodiments, the subject is female. In some specific embodiments, the subject is male.

In some embodiments, the subject presents with elevated expression of FRalpha. In some specific embodiments, the subject presents with cancer, and cells of the cancer express an elevated concentration of FRalpha.

In some embodiments, the method comprises identifying that the subject comprises cells that express FRalpha.

In some embodiments, the subject presents with cancer. In some specific embodiments, the subject presents with cancer, and the cancer comprises cells that express FRalpha. In some very specific embodiments, the subject presents with cancer, and the cancer comprises cells that express an aberrantly high concentration of FRalpha. The cancer cells, for example, may overexpress FRalpha.

In some embodiments, the cancer is selected from ovarian cancer, fallopian tube cancer, primary peritoneal cancer, endometrial cancer, breast cancer, lung cancer, adenocarcinoma, mesothelioma, colorectal cancer, brain cancer, and acute myeloid leukemia. In some specific embodiments, the cancer is non-small cell lung cancer, adenocarcinoma, mesothelioma, triple-negative breast cancer, epithelial ovarian cancer, fallopian tube cancer, primary peritoneal cancer, or acute myeloid leukemia.

In some embodiments, the administering is selected from intravenous, intramuscular, subcutaneous, intradermal, intraocular, parenteral, intraperitoneal, intrathecal, intralesional, and intratumoral administration. In some specific embodiments, the administering is intravenous administration.

Various aspects of this disclosure relate to a recombinant nucleic acid encoding a recombinant anti-FRalpha antibody or antigen-binding fragment thereof as described anywhere in this disclosure.

Various aspects of this disclosure relate to a recombinant nucleic acid, comprising a nucleotide sequence that encodes a protein that comprises an antigen-binding region, wherein (1) the antigen-binding region comprises a first variable domain and a second variable domain; (2) the first variable domain comprises a VH CDR1 region comprising an amino acid sequence that is identical to at least 7, 8, 9, or 10 consecutive amino acids of SEQ ID NO: 5, a VH CDR2 region comprising an amino acid sequence that is identical to at least 7, 8, 9, 10, 11, 12, 13, 14, 15, 16, or 17 consecutive amino acids of SEQ ID NO: 6, and a VH CDR3 region comprising an amino acid sequence that is identical to at least 7, 8, 9, 10, or 11 consecutive amino acids of SEQ ID NO: 7; (3) the second variable domain comprises a VL CDR1 region comprising an amino acid sequence that is identical to at least 7, 8, 9, 10, or 11 consecutive amino acids of SEQ ID NO: 8, a VL CDR2 region comprising an amino acid sequence that is identical to at least 3, 4, 5, 6, or 7 consecutive amino acids of SEQ ID NO: 9, and a VL CDR3 region comprising an amino acid sequence that is identical to at least 3, 4, 5, 6, 7, 8, 9, or 10 consecutive amino acids of SEQ ID NO: 10; and (4) the first variable domain and the second variable domain are paired in the antigen-binding region of the protein such that the antigen-binding region specifically binds human FRalpha.

In some embodiments, the first variable domain comprises an amino acid sequence that has at least 90 percent sequence homology with SEQ ID NO: 3. In some specific embodiments, the first variable domain comprises an amino acid sequence that has at least 95 percent sequence homology with SEQ ID NO: 3. In some even more specific embodiments, the first variable domain comprises an amino acid sequence that has at least 98 percent sequence homology with SEQ ID NO: 3. In some very specific embodiments, the first variable domain comprises an amino acid sequence that has at least 99 percent sequence homology with SEQ ID NO: 3.

In some embodiments, the first variable domain comprises an amino acid sequence that has at least 90 percent sequence identity with SEQ ID NO: 3. In some specific embodiments, the first variable domain comprises an amino acid sequence that has at least 95 percent sequence identity with SEQ ID NO: 3. In some even more specific embodiments, the first variable domain comprises an amino acid sequence that has at least 99 percent sequence identity with SEQ ID NO: 3. In some very specific embodiments, the first variable domain comprises an amino acid sequence that is identical to SEQ ID NO: 3.

In some embodiments, the second variable domain comprises an amino acid sequence that has at least 90 percent sequence homology with SEQ ID NO: 4. In some specific embodiments, the second variable domain comprises an amino acid sequence that has at least 95 percent sequence homology with SEQ ID NO: 4. In some even more specific embodiments, the second variable domain comprises an amino acid sequence that has at least 98 percent sequence homology with SEQ ID NO: 4. In some very specific embodiments, the second variable domain comprises an amino acid sequence that has at least 99 percent sequence homology with SEQ ID NO: 4.

In some embodiments, the second variable domain comprises an amino acid sequence that has at least 90 percent sequence identity with SEQ ID NO: 4. In some specific embodiments, the second variable domain comprises an amino acid sequence that has at least 95 percent sequence identity with SEQ ID NO: 4. In some even more specific embodiments, the second variable domain comprises an amino acid sequence that has at least 99 percent sequence identity with SEQ ID NO: 4. In some very specific embodiments, the second variable domain comprises an amino acid sequence that is identical to SEQ ID NO: 4.

In some embodiments, the first variable domain comprises an amino acid sequence that has at least 90 percent sequence homology with SEQ ID NO: 3, and the second variable domain comprises an amino acid sequence that has at least 90 percent sequence homology with SEQ ID NO: 4. In some specific embodiments, the first variable domain comprises an amino acid sequence that has at least 95 percent sequence homology with SEQ ID NO: 3, and the second variable domain comprises an amino acid sequence that has at least 95 percent sequence homology with SEQ ID NO: 4. In some even more specific embodiments, the first variable domain comprises an amino acid sequence that has at least 98 percent sequence homology with SEQ ID NO: 3, and the second variable domain comprises an amino acid sequence that has at least 99 percent sequence homology with SEQ ID NO: 4. In some very specific embodiments, the first variable domain comprises an amino acid sequence that has at least 99 percent sequence homology with SEQ ID NO: 3, and the second variable domain comprises an amino acid sequence that has at least 99 percent sequence homology with SEQ ID NO: 4.

In some embodiments, the first variable domain comprises an amino acid sequence that has at least 90 percent sequence identity with SEQ ID NO: 3, and the second variable domain comprises an amino acid sequence that has at least 90 percent sequence identity with SEQ ID NO: 4. In some specific embodiments, the first variable domain comprises an amino acid sequence that has at least 95 percent sequence identity with SEQ ID NO: 3, and the second variable domain comprises an amino acid sequence that has at least 95 percent sequence identity with SEQ ID NO: 4. In some even more specific embodiments, the first variable domain comprises an amino acid sequence that has at least 99 percent sequence identity with SEQ ID NO: 3, and the second variable domain comprises an amino acid sequence that has at least 99 percent sequence identity with SEQ ID NO: 4. In some very specific embodiments, the first variable domain comprises an amino acid sequence that is identical to SEQ ID NO: 3, and the second variable domain comprises an amino acid sequence that is identical to SEQ ID NO: 4.

Various aspects of this disclosure relate to a recombinant nucleic acid, comprising a nucleotide sequence that encodes a protein that comprises an antigen-binding region, wherein (1) the antigen-binding region comprises a first variable domain and a second variable domain; (2) the first variable domain comprises an amino acid sequence that has at least 90 percent sequence homology with SEQ ID NO: 3 (such as at least 95, 97, 98, or 99 percent sequence homology); (3) the second variable domain comprises an amino acid sequence that has at least 90 percent sequence homology with SEQ ID NO: 4 (such as at least 95, 97, 98, or 99 percent sequence homology); and (4) the antibody or antigen-binding fragment thereof binds human FRalpha.

In some embodiments, the first variable domain comprises an amino acid sequence that has at least 90 percent sequence identity with SEQ ID NO: 3 (such as at least 95, 97, 98, or 99 percent sequence identity), and the second variable domain comprises an amino acid sequence that has at least 90 percent sequence identity with SEQ ID NO: 4 (such as at least 95, 97, 98, or 99 percent sequence identity).

In some embodiments, the protein is a recombinant anti-FRalpha antibody as described anywhere in this disclosure.

In some embodiments, the protein is an antigen-binding fragment of a recombinant anti-FRalpha antibody as described anywhere in this disclosure.

In some embodiments, the protein is an IgG-like bispecific antibody or portion thereof as described anywhere in this disclosure. In some specific embodiments, the protein is a trifunctional antibody or portion thereof as described anywhere in this disclosure. IgG-like bispecific antibodies such as trifunctional antibodies may be encoded, for example, by two different nucleic acids such as a first nucleic acid that encodes a first heavy and light chain that binds a first epitope (such as FRalpha) and a second nucleic acid that encodes a second heavy and light chain that binds a second epitope (such as a CD3) for expression of the first heavy and light chain in a first cell line and expression of the second heavy and light chain in a second cell line to avoid the pairing of heavy and light chains that bind different epitopes.

In some embodiments, the protein is a bi-specific T-cell engager (BiTE). A BiTE is a fusion protein comprising a scFV that binds an antigen (for example, FRalpha) and a domain that binds a cell-surface protein expressed by a T-cell such as CD3. Examples of BiTEs include blinatumomab (also known as BLINCYTO®) and tebentafusp (also known as KIMMTRAK®). Those of ordinary skill are capable of designing BiTEs that bind FRalpha and CD3, for example, by replacing the variable regions that bind CD19 in blinatumomab or glycoprotein 100 in tebentafusp with the variable regions set forth in SEQ ID NOs: 3 and 4 (see, for example, U.S. Pat. Nos. 10,517,960 and 11,597,766, which are incorporated by reference in their entirety).

In some embodiments, the protein is a chimeric antigen receptor (CAR). A CAR is a fusion protein comprising (1) an N-terminal, extracellular scFV that binds an antigen (for example, FRalpha), (2) a transmembrane alpha-helix, and (3) a C-terminal, intracellular signaling domain such as CD3-zeta and/or one or more intracellular signaling domains selected from CD27, CD28, CD134, and CD137. The intracellular signaling domain typically comprises an immunoreceptor tyrosine-based activation motif (ITAM). Examples of CARs include tisagenlecleucel (also known as KYMRIAH®) and axicabtagene ciloleucel (also known as YESCARTA®). Those of ordinary skill are capable of designing CARs that bind FRalpha, for example, by replacing the variable regions that bind CD19 in tisagenlecleucel or axicabtagene ciloleucel with the variable regions set forth in SEQ ID NOs: 3 and 4 (see, for example, U.S. Pat. Nos. 7,446,190, 7,741,465, and 9,499,629, which are incorporated by reference in their entirety).

In some embodiments, the recombinant nucleic acid comprises a nucleotide sequence that is at least 70 percent identical to SEQ ID NO: 1. In some specific embodiments, the recombinant nucleic acid comprises a nucleotide sequence that is at least 80 percent identical to SEQ ID NO: 1. In some even more specific embodiments, the recombinant nucleic acid comprises a nucleotide sequence that is at least 90 percent identical to SEQ ID NO: 1. In some very specific embodiments, the recombinant nucleic acid comprises a nucleotide sequence that is at least 95 percent identical to SEQ ID NO: 1.

In some embodiments, the recombinant nucleic acid comprises a nucleotide sequence that encodes an amino acid sequence that has at least 90 percent sequence homology with SEQ ID NO: 11. In some specific embodiments, the recombinant nucleic acid comprises a nucleotide sequence that encodes an amino acid sequence that has at least 95 percent sequence homology with SEQ ID NO: 11. In some even more specific embodiments, the recombinant nucleic acid comprises a nucleotide sequence that encodes an amino acid sequence that has at least 98 percent sequence homology with SEQ ID NO: 11. In some very specific embodiments, the recombinant nucleic acid comprises a nucleotide sequence that encodes an amino acid sequence that has at least 99 percent sequence homology with SEQ ID NO: 11.

In some embodiments, the recombinant nucleic acid comprises a nucleotide sequence that encodes an amino acid sequence that is at least 90 percent identical to SEQ ID NO: 11. In some specific embodiments, the recombinant nucleic acid comprises a nucleotide sequence that encodes an amino acid sequence that is at least 95 percent identical to SEQ ID NO: 11. In some even more specific embodiments, the recombinant nucleic acid comprises a nucleotide sequence that encodes an amino acid sequence that is at least 98 percent identical to SEQ ID NO: 11. In some very specific embodiments, the recombinant nucleic acid comprises a nucleotide sequence that encodes an amino acid sequence that is at least 99 percent identical to SEQ ID NO: 11.

In some embodiments, the recombinant nucleic acid comprises a nucleotide sequence that is at least 70 percent identical to SEQ ID NO: 2. In some specific embodiments, the recombinant nucleic acid comprises a nucleotide sequence that is at least 80 percent identical to SEQ ID NO: 2. In some even more specific embodiments, the recombinant nucleic acid comprises a nucleotide sequence that is at least 90 percent identical to SEQ ID NO: 2. In some very specific embodiments, the recombinant nucleic acid comprises a nucleotide sequence that is at least 95 percent identical to SEQ ID NO: 2.

In some embodiments, the recombinant nucleic acid comprises a nucleotide sequence that encodes an amino acid sequence that has at least 90 percent sequence homology with SEQ ID NO: 12. In some specific embodiments, the recombinant nucleic acid comprises a nucleotide sequence that encodes an amino acid sequence that has at least 95 percent sequence homology with SEQ ID NO: 12. In some even more specific embodiments, the recombinant nucleic acid comprises a nucleotide sequence that encodes an amino acid sequence that has at least 98 percent sequence homology with SEQ ID NO: 12. In some very specific embodiments, the recombinant nucleic acid comprises a nucleotide sequence that encodes an amino acid sequence that has at least 99 percent sequence homology with SEQ ID NO: 12.

In some embodiments, the recombinant nucleic acid comprises a nucleotide sequence that encodes an amino acid sequence that is at least 90 percent identical to SEQ ID NO: 12. In some specific embodiments, the recombinant nucleic acid comprises a nucleotide sequence that encodes an amino acid sequence that is at least 95 percent identical to SEQ ID NO: 12. In some even more specific embodiments, the recombinant nucleic acid comprises a nucleotide sequence that encodes an amino acid sequence that is at least 98 percent identical to SEQ ID NO: 12. In some very specific embodiments, the recombinant nucleic acid comprises a nucleotide sequence that encodes an amino acid sequence that is at least 99 percent identical to SEQ ID NO: 12.

In some embodiments, the recombinant nucleic acid comprises an origin of replication, wherein the recombinant nucleic acid is a plasmid.

Various aspects of this disclosure relate to a viral vector, comprising the recombinant nucleic acid as described anywhere in this disclosure. In some embodiments, the vector has a tropism for human leukocytes. In some specific embodiments, the vector has a tropism for human T-cells, natural killer cells, or monocytes. In some very specific embodiments, the viral vector is an adenovirus vector, an adeno-associated virus vector, a lentiviral vector, or a gamma-retroviral vector. Viral vectors may be used, for example, to introduce a recombinant nucleic acid encoding a CAR into a leukocyte to produce a transgenic leukocyte that expresses the CAR for use as a cancer immunotherapy.

Various aspects of this disclosure relate to a cell, comprising a recombinant nucleic acid as described anywhere in this disclosure or a viral vector as described anywhere in this disclosure.

In some embodiments, the cell is a prokaryote such as *E. coli*, and the cell is used for cloning or propagating the recombinant nucleic acid. When the cell is a prokaryote, then the recombinant nucleic acid generally includes an origin of replication for propagation as well as an antibiotic resistance gene to provide a selective advantage for cells that comprise the recombinant nucleic acid.

In some embodiments, the cell is a bacterial cell.

In some embodiments, the cell is mammalian cell. In some specific embodiments, the cell is an immortalized mammalian cell line. In some very specific embodiments, the cell is a CHO cell (Chinese hamster ovary), a HEK cell (human embryonic kidney), such as a HEK293 cell, a NSO cell (murine myeloma cell), a Sp2/0 cell (murine myeloma cell), or a PER.C6® cell (human retina cell). Immortalized mammalian cell lines are generally used to express proteins for use as therapeutics such as therapeutic antibodies (including, for example, the human anti-FRalpha antibody described herein). Mammalian cells generally ensure the fidelity of the tertiary and quaternary structure of the variable regions and other regions of an FRalpha-binding protein as well as the fidelity of post-translational modifications such as glycosylation patterns. Mammalian cells may also be used, for example, to manufacture viral vectors as described herein. The recombinant nucleic acid may be present in the cell either transiently or stably.

In some embodiments, the cell is a mammalian cell, and the mammalian cell expresses the protein.

In some embodiments, the cell is a mammalian cell, the mammalian cell expresses a viral vector, and the recombinant nucleic acid comprises a packaging signal for packaging the recombinant nucleic acid in the viral vector.

In some embodiments, the cell is a tissue culture cell. In some specific embodiments, the cell is a tissue culture cell, and the tissue culture cell expresses the protein. In some specific embodiments, the cell is a tissue culture cell; the tissue culture cell expresses a viral vector; and the recombinant nucleic acid comprises a packaging signal for packaging the recombinant nucleic acid in the viral vector.

In some embodiments, the cell is a peripheral blood mononuclear cell (PBMC). In some specific embodiments the cell is a human PBMC. In some specific embodiments, the cell is a T-cell, a natural killer cell, a monocyte, a macrophage, or a dendritic cell. In some very specific embodiments, the cell is a human T-cell, a human natural killer cell, a human monocyte, a human macrophage, or a human dendritic cell. PBMCs may be transfected with a recombinant nucleic acid to express a CAR such that the PBMCs may be used as a cancer immunotherapy, for example, such as a CAR-T cell, a CAR-NK cell, CAR-monocyte, CAR-macrophage, or CAR-DC.

In some embodiments, the cell is a leukocyte, and the nucleotide sequence encodes a protein that is a CAR. In some specific embodiments, the cell is a human leukocyte, and the nucleotide sequence encodes a protein that is a CAR. In some very specific embodiments, the cell is a human leukocyte, the nucleotide sequence encodes a protein that is a CAR, and the human leukocyte expresses the CAR.

In some embodiments, the cell is a PBMC, and the nucleotide sequence encodes a protein that is a CAR. In some specific embodiments, the cell is a human PBMC, and the nucleotide sequence encodes a protein that is a CAR. In some very specific embodiments, the cell is a human PBMC, the nucleotide sequence encodes a protein that is a CAR, and the human PBMC expresses the CAR.

In some embodiments, the cell is a T-cell, a natural killer cell, a monocyte, a macrophage, or a dendritic cell, and the nucleotide sequence encodes a protein that is a CAR. In some specific embodiments, the cell is a human T-cell, a human natural killer cell, a human monocyte, a human macrophage, or a human dendritic cell, and the nucleotide sequence encodes a protein that is a CAR. In some very specific embodiments, the cell is a human T-cell, a human natural killer cell, a human monocyte, a human macrophage, or a human dendritic cell, the nucleotide sequence encodes a protein that is a CAR, and the cell expresses the CAR.

Various aspects of this disclosure relate to a Fab fragment that binds FRalpha and that comprises CDRs that have sequence homology with the amino acid sequences set forth in SEQ ID NO: 5-10. A Fab may comprise amino acid sequences that have, for example, at least 90, 95, 97, 98, or 99 percent sequence homology with the sequences set forth in SEQ ID NO: 5-10 or at least 90, 95, 97, 98, or 99 percent sequence identity with the sequences set forth in SEQ ID NO: 5-10. In some embodiments, the Fab fragment is encoded by a recombinant nucleic acid as described anywhere in this disclosure.

Various aspects of this disclosure relate to a Fab fragment that binds FRalpha and that comprises variable domains that have sequence homology with the amino acid sequences set forth in SEQ ID NO: 3 and 4. A Fab may comprise amino acid sequences that have, for example, at least 90, 95, 97, 98, or 99 percent sequence homology with the sequences set forth in SEQ ID NO: 3 and 4 or at least 90, 95, 97, 98, or 99 percent sequence identity with the sequences set forth in SEQ ID NO: 3 and 4. In some embodiments, the Fab fragment is encoded by a recombinant nucleic acid as described anywhere in this disclosure.

Various aspects of this disclosure relate to an antibody comprising a Fab fragment described anywhere in this disclosure. In some embodiments, the antibody is encoded by a recombinant nucleic acid as described anywhere in this disclosure.

Various aspects of this disclosure relate to a bi-specific antibody that comprises CDRs that have sequence homology with the amino acid sequences set forth in SEQ ID NO: 5-10. A bi-specific antibody may comprise amino acid sequences that have, for example, at least 90, 95, 97, 98, or 99 percent sequence homology with the sequences set forth in SEQ ID NO: 5-10 or at least 90, 95, 97, 98, or 99 percent sequence identity with the sequences set forth in SEQ ID NO: 5-10. In some embodiments, the bi-specific antibody is encoded by a recombinant nucleic acid as described anywhere in this disclosure.

In some embodiments, the bi-specific antibody comprises variable domains that have sequence homology with the amino acid sequences set forth in SEQ ID NO: 3 and 4. A bi-specific antibody may comprise amino acid sequences that have, for example, at least 90, 95, 97, 98, or 99 percent sequence homology with the sequences set forth in SEQ ID NO: 3 and 4 or at least 90, 95, 97, 98, or 99 percent sequence identity with the sequences set forth in SEQ ID NO: 3 and 4. In some embodiments, the bi-specific antibody is encoded by a recombinant nucleic acid as described anywhere in this disclosure.

Various aspects of this disclosure relate to a BiTE that comprises CDRs that have sequence homology with the amino acid sequences set forth in SEQ ID NO: 5-10. A BiTE may comprise amino acid sequences that have, for example, at least 90, 95, 97, 98, or 99 percent sequence homology with the sequences set forth in SEQ ID NO: 5-10 or at least 90, 95, 97, 98, or 99 percent sequence identity with the sequences set forth in SEQ ID NO: 5-10. In some embodiments, the BiTE is encoded by a recombinant nucleic acid as described anywhere in this disclosure.

In some embodiments, the BiTE comprises CDRs that have sequence homology with the amino acid sequences set forth in SEQ ID NO: 3 and 4. A BiTE may comprise amino acid sequences that have, for example, at least 90, 95, 97, 98, or 99 percent sequence homology with the sequences set forth in SEQ ID NO: 3 and 4 or at least 90, 95, 97, 98, or 99 percent sequence identity with the sequences set forth in SEQ ID NO: 3 and 4. In some embodiments, the BiTE is encoded by a recombinant nucleic acid as described anywhere in this disclosure.

Having described various features of this disclosure both generally and specifically in the preceding detailed description, the following exemplification provides a specific example of the preparation of the subject matter described herein. By way of this example, and in the context of the preceding detailed description, the skilled person will immediately recognize variations to the method set forth in the example (such as by engineering a BiTE, scFv, or chimeric antigen receptor instead of an IgG). The following exemplification is illustrative only and shall not limit this disclosure or any patent claim that matures from this disclosure. Any patent claim that matures from this disclosure shall instead be limited by the explicit features recited in the claim in the context of its claim dependency and according to conventional principles of claim construction as applied in view of this disclosure.

EXEMPLIFICATION

The Example. Identification of CDRs that Display High Affinity for FRalpha Extracellular Domain and a Corresponding Fully-Human Anti-FRalpha IgG1 Antibody A Fab phage display library was constructed from peripheral blood obtained from 120 healthy human donors. Briefly, this library was constructed by randomly combining nucleotide sequences encoding immunoglobulin heavy chain variable regions with nucleotide sequences encoding immunoglobulin light chain variable regions. The library had a diversity of approximately 1 trillion combinations. Bio-panning of the library identified 226 positive clones that bound both human and cynomolgus FRalpha. Each of the 226 positive clones was sequenced, and 131 unique clones were identified, of which 35 were available for full-length antibody construction.

Figure 1:
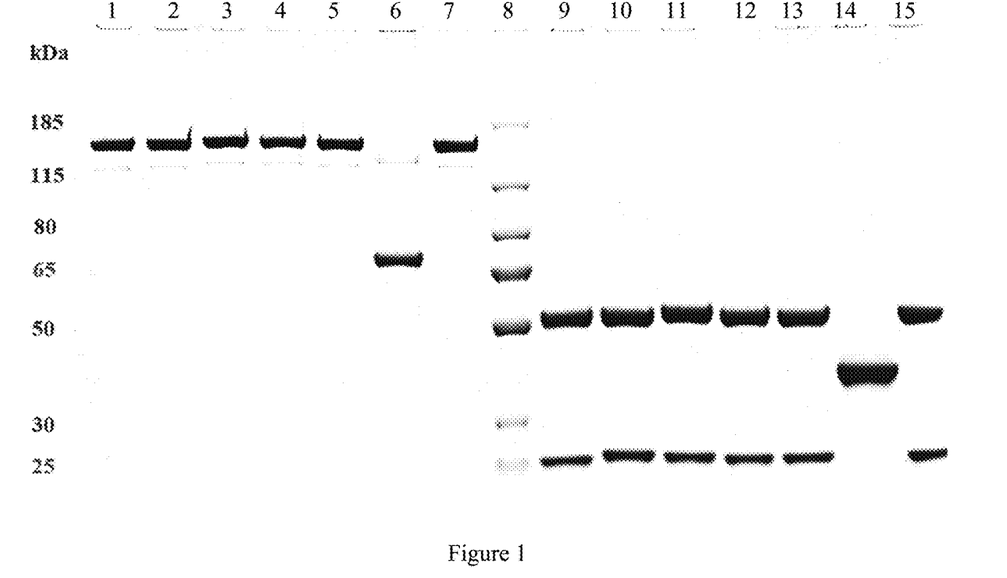
FIG. 1 is an image of a Coomassie-blue stained sodium dodecyl sulfate polyacrylamide gel electrophoresis (SDS-PAGE) gel loaded with five anti-FRalpha IgG antibodies under non-reducing conditions (lanes 1-5), and IgG standard under non-reducing conditions (lane 7), a molecular weight standard (lane 8), the five anti-FRalpha IgG antibodies under reducing conditions (lanes 9-13), and the IgG standard under reducing conditions (lane 15).

The VH and VL nucleotide sequences of 14 colonies were independently cloned into a human IgG1 heavy chain gene and a human kappa light chain gene for expression of human IgGis. A representative image of an SDS-PAGE gel is depicted in FIG. 1, which demonstrates successful cloning and expression. Lanes 1-5 each contain 1 microgram of a different IgG1s loaded under non-reducing conditions, lane 7 contains 1 microgram of an IgG standard loaded under non-reducing conditions, lane 8 contains a molecular weight standard, lanes 9-13 each contain 2 micrograms of different IgG1s loaded under reducing conditions, and lane 15 contains 2 micrograms of the IgG standard loaded under reducing conditions. Lanes 1 and 9 correspond to an IgG1 with sequences set forth in SEQ ID NO: 3-12.

Figure 2:
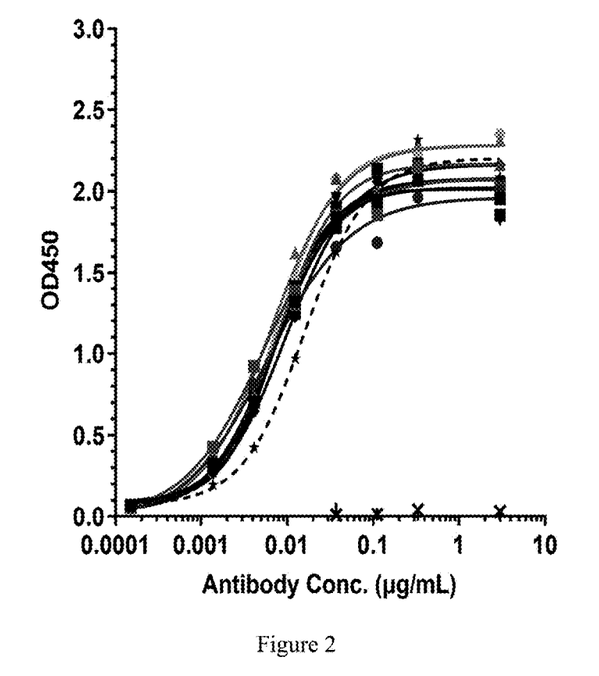
FIG. 2 is a graph that depicts the binding of various anti-FRalpha IgG antibodies to human FRalpha extracellular domain as assessed by enzyme-linked immunosorbent assay (ELISA). The dashed line depicts binding of the control anti-FRalpha IgG mirvetuximab.

The affinity of each IgG1 for FRalpha was confirmed by ELISA. Briefly, a fusion protein containing the extracellular domain of human FRalpha and a polyhistidine tag was used to coat ELISA plates, which were washed three times with phosphate-buffered saline (PBS) containing 0.1 percent polysorbate 20 (PBST), then blocked with PBS containing 5 percent powdered milk (PBSM), and then washed three more times with PBST. Wells were then incubated with antibodies at varying concentrations for 60 minutes at room temperature in 1 percent PBSM. Wells were then washed three times with PBST, after which the secondary, horse-radish-peroxidase-conjugated antibody anti-human-IgG-Fc-HRP (ab97225, Abcam, United Kingdom) was added at a 1:8000 dilution in 1 percent PBSM for 50 minutes at room temperature. The wells were then washed six times with PBST, after which 3,3',5,5"-tetramethylbenzidine (TMB) was added. The reaction was stopped with 2 molar sulfuric acid, and the TMB diamine product was quantified at 450 nanometers in a plate reader. Results are depicted in FIG. 2. The antibody according to SEQ ID NO: 3-12 displayed a half maximal effective concentration (EC50) of 7.149 nanograms per milliliter (about 50 picomolar). A second anti-FRalpha antibody identified by bio-panning displayed an EC50 of 5.547 nanograms per milliliter (about 40 picomolar). Mirvetuximab was assessed as a positive control and displayed an EC50 of 18.53 nanograms per milliliter (about 120 picomolar).

Figure 3:
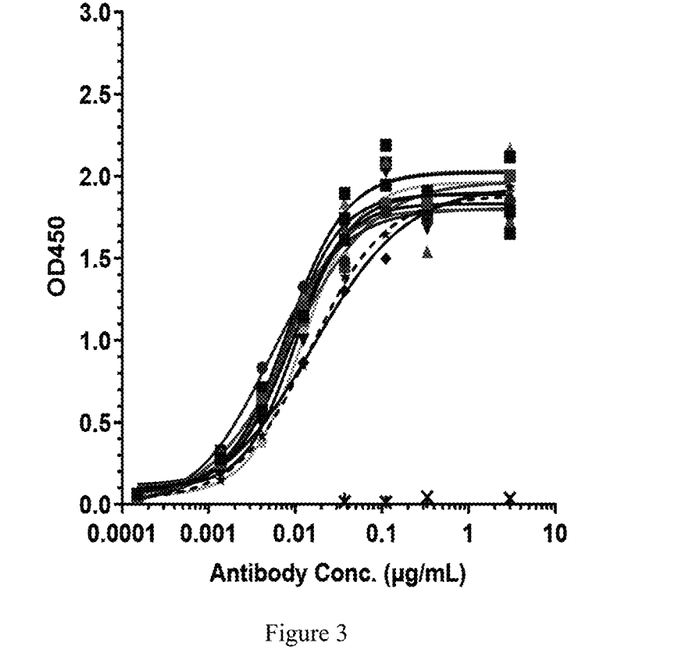
FIG. 3 is a graph that depicts the binding of various anti-FRalpha IgG antibodies to cynomolgus FRalpha extracellular domain as assessed by ELISA. The dashed line depicts binding of the control anti-FRalpha IgG mirvetuximab.

The ELISA of the preceding paragraph was repeated with a fusion protein containing the extracellular domain of cynomolgus FRalpha and a polyhistidine tag. Results are depicted in FIG. 3. The antibody according to SEQ ID NO: 3-12 displayed an EC50 of 8.028 nanograms per milliliter (about 60 picomolar). The second anti-FRalpha antibody displayed an EC50 of 8.833 nanograms per milliliter (about 60 picomolar). Mirvetuximab displayed an EC50 of 23.26 nanograms per milliliter (about 160 picomolar).

Figure 4:
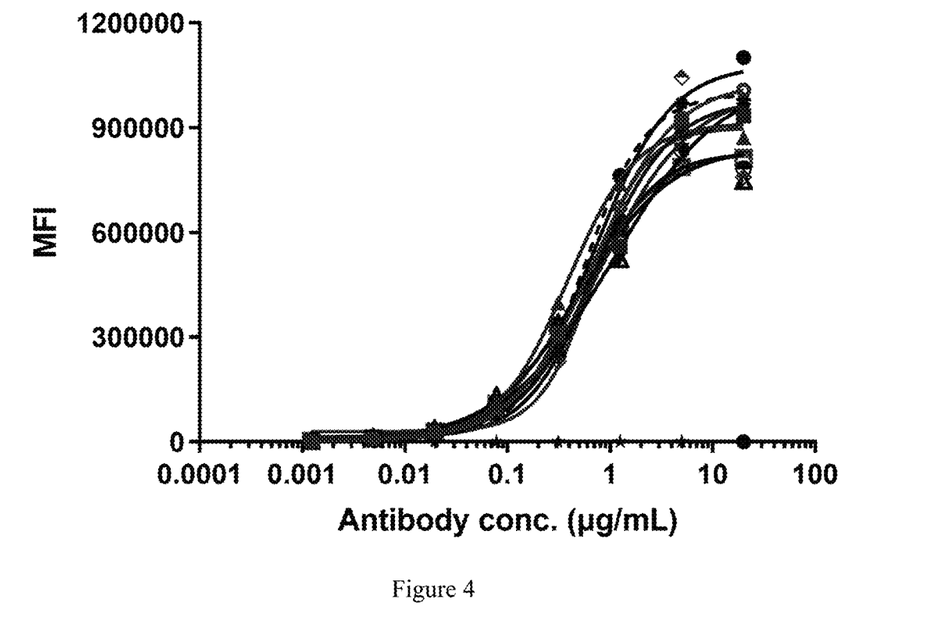
FIG. 4 is a graph that depicts the binding of various anti-FRalpha IgG antibodies to HEK293 cells that express human FRalpha as assessed by flow cytometry. The dashed line depicts binding of the control anti-FRalpha IgG mirvetuximab.

The affinity of each antibody was then assessed by flow cytometry. Briefly, HEK293 cells transfected to express FRalpha were washed with fluorescence-activated cell sorting (FACS) buffer, to which the IgGs were added at varying concentrations and incubated at 4 degrees Celsius for 60 minutes. The cells were then centrifuged and washed twice in FACS buffer. A phycoerythrin-labelled anti-human IgG, Fcgamma antibody (109-115-098; Jackson ImmunoResearch, Pennsylvania, United States) was then added to the cells at a 1:200 dilution and incubated at 4 degrees Celsius for 30 minutes. The cells were then washed, resuspended in FACS buffer, and counted by flow cytometry. Results are depicted in FIG. 4. The antibody according to SEQ ID NO: 3-12 displayed an EC50 of 687.5 nanograms per milliliter (about 5 nanomolar). The second antibody displayed an EC50 of 737.0 nanograms per milliliter (about 5 nanomolar). Mirvetuximab was assessed as a positive control and displayed an EC50 of 563.9 nanograms per milliliter (about 4 nanomolar).

Figure 5A:
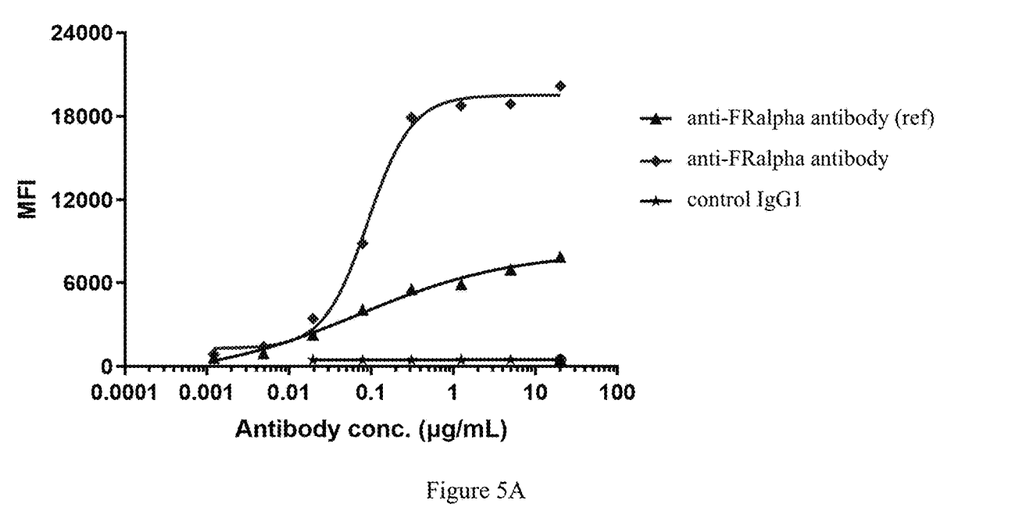
FIG. 5A is a graph that depicts the binding of the anti-FRalpha IgG of this disclosure (♦), a reference anti-FRalpha IgG (▲), and a control IgG (★) to human ovarian cancer SKOV3 cells that express human FRalpha as assessed by flow cytometry.
Figure 5B:
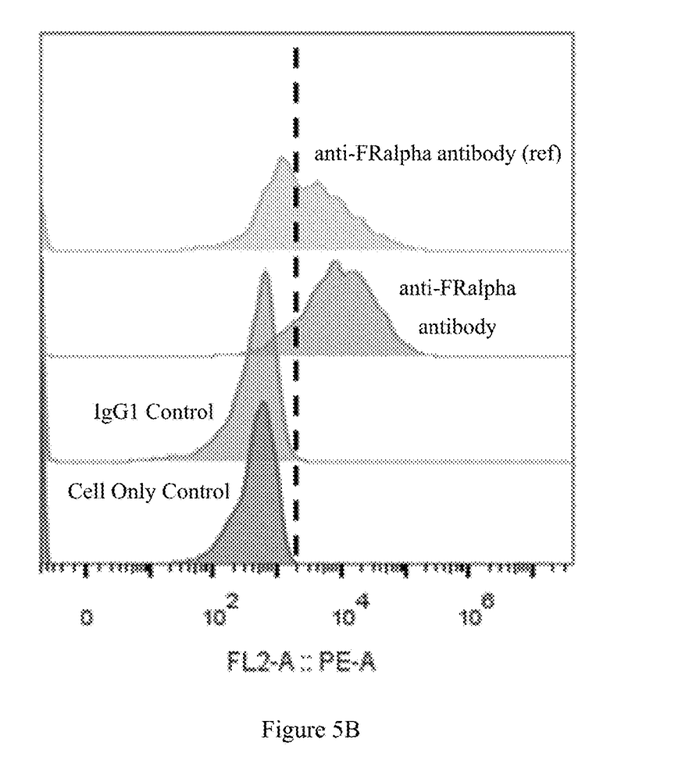
FIG. 5B contains flow cytometry traces for cell counts monitored by a channel assessing phycoerythrin-associated fluorescence of a secondary antibody for primary antibodies selected from the anti-FRalpha IgG of this disclosure, a reference anti-FRalpha IgG, and a control IgG as well as a cell-only control. The cells were human ovarian cancer cells that express human FRalpha, namely, SKOV3 cells.

The flow cytometry experiment of the preceding paragraph was repeated with a human ovarian cancer cell line that expresses FRalpha, SKOV3. Results are depicted in FIGS. 5A and 5B. The antibody according to SEQ ID NO: 3-12 displayed a sub-nanomolar EC50 (♦), and the second antibody did not perform as well (▲). The antibody according to SEQ ID NO: 3-12 was then designated the lead antibody for further development.

The nucleotide sequences of the human VH and VL regions of the lead antibody are set forth in Table 1 below. The variable regions have the amino acid sequences set forth in Table 2 below and the CDRs set forth in Table 3 below. In the context of the IgG1, the lead antibody has a heavy chain and light chain according to the amino acid sequences set forth in Table 4 below. This IgG1 has a molecular weight of about 143.84 kilodaltons, an isoelectric point of about 8.52, and it was capable of purification to purities greater than 95 percent as assessed by SDS-PAGE, size exclusion chromatography, and HPLC.

TABLE 1

Nucleotide sequences of the variable domains of the lead anti-FRalpha antibody

| SEQ ID NO. | Region | Sequence |
|---|---|---|
| 1 | VH | GAGGTGCAGCTGTTGGAGTCTGGGGGAGGCTTGGTCAAGCCTGGGGGGTC<br>CCTGAGACTCTCCTGTGCAGCCTCTGGATTCACCTTCAGTAGCTATACCA<br>TGAACTGGGTCCGCCAGGCTCCAGGGAAGGGGCTGGAATGGGTCTCATCC<br>ATTAGTAGTGGTGGTGGTTACATATACTACGCAGACTCAGTGAAGGACCG<br>ATTCACCATCTCCAGAGACAACGCCAAGAACTCACTGTATCTGCAAATGA<br>ACAGCCTGCGAGCCGAGGACACGGCCGTGTATTACTGTGCAAAAGGGGAT<br>ACGATCATGATAATATCGGCGTGGGGCCAAGGGACAACGGTCACCGTCTC<br>ATCA |
| 2 | VL | GACATCCAGTTGACCCAGTCTCCTTCCACCCTGTCTGCATCTGTAGGAGA<br>CAGAGTCACCATCACTTGCCGGGCCAGTCAGAGTATTAGTAGTTGGTTGG<br>CCTGGCATCAGCAGAAACCAGGGAAAGCCCCTAAACTCCTCATCTATGCT<br>GCATCCAGTTTGCAAATGGGGTCCCATCAAGGTTCAGCGGCAGTGGATT<br>TGGGACAGATTTCACTCTCACCATCAGCAGCCTGCAGCCTGAAGACTTTG<br>CAACTTACTATTGTCAACAGGCTAGCAGTTTCCCTCTCACTTTCGGCGGA<br>GGGACCAAGGTGGAGATCAAA |

TABLE 2

Amino acid sequences of the variable domains of the lead anti-FRalpha antibody

| SEQ ID NO. | Region | Sequence |
|---|---|---|
| 3 | VH | EVQLLESGGGLVKPGGSLRLSCAASGFTFSSYTMNWVRQAPGKGLEWVSS<br>ISSGGGYIYYADSVKDRFTISRDNAKNSLYLQMNSLRAEDTAVYYCAKGD<br>TIMIISAWGQGTTVTVSS |
| 4 | VL | DIQLTQSPSTLSASVGDRVTITCRASQSISSWLAWHQQKPGKAPKLLIYA<br>ASSLQNGVPSRFSGSGFGTDFTLTISSLQPEDFATYYCQQASSFPLTFGG<br>GTKVEIK |

TABLE 3

Amino acid sequences of the CDRs of the lead anti-FRalpha antibody

| SEQ ID NO. | Region | Sequence |
|---|---|---|
| 5 | VH CDR1 | GFTFSSYTMN |
| 6 | VH CDR2 | SISSGGGYIYYADSVKD |
| 7 | VH CDR3 | AKGDTIMIISA |
| 8 | VL CDR1 | RASQSISSWLA |
| 9 | VL CDR2 | AASSLQN |
| 10 | VL CDR3 | QQASSFPLTF |

TABLE 4

Amino Acid Sequences of lead fully-human anti-FRalpha IgG1 antibody

| SEQ ID NO. | Region | Sequence |
|---|---|---|
| 11 | Full Heavy Chain | EVQLLESGGGLVKPGGSLRLSCAASGFTFSSYTMNWVRQAPGKGLEWVSS<br>ISSGGGYIYYADSVKDRFTISRDNAKNSLYLQMNSLRAEDTAVYYCAKGD<br>TIMIISAWGQGTTVTVSSASTKGPSVFPLAPSSKSTSGGTAALGCLVKDY<br>FPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVY |

TABLE 4-continued

Amino Acid Sequences of lead fully-human anti-FRalpha IgG1 antibody

| SEQ ID NO. | Region | Sequence  10        20        30        40<br>12345678901234567890123456789012345678901234567890 |
|---|---|---|
|  |  | TLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPGK |
| 12 | Full Light Chain | DIQLTQSPSTLSASVGDRVTITCRASQSISSWLAWHQQKPGKAPKLLIYA<br>ASSLQNGVPSRFSGSGFGTDFTLTISSLQPEDFATYYCQQASSFPLTFGG<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSENRGEC |

No patent claim that matures from this disclosure shall be interpreted as requiring any feature of the foregoing Example. Any methods described in the claims or specification shall not be interpreted to require the steps to be performed in a specific order unless expressly stated otherwise. The methods shall be interpreted to provide support to perform the recited steps in any order unless expressly stated otherwise.

Certain features described in the context of separate implementations can also be implemented in combination in a single implementation. Conversely, various features that are described in the context of a single implementation can also be implemented in multiple implementations separately or in any suitable sub-combination. Moreover, although features may be described above in certain combinations and even initially claimed as such, one or more features from a claimed combination can be excised from the combination, and the claimed combination may be directed to a sub-combination or variation of a sub-combination.

The example configurations described in this document do not represent all the examples that may be implemented or that fall within the scope of the claims. The term "example" shall be interpreted to mean "serving as an example, instance, or illustration," and not "preferred" or "advantageous over other examples."

Articles such as "the," "a," and "an" can connote the singular or plural. The word "or" when used without a preceding "either" (or other similar language indicating that "or" is unequivocally meant to be exclusive, for example, only one of x or y) shall be interpreted to be inclusive (for example, "x or y" means one or both of x and y).

The term "and/or" shall also be interpreted to be inclusive (for example, "x and/or y" means one or both of x and y). In situations where "and/or" or "or" are used as a conjunction for a group of three or more items, then the group shall be interpreted to include one item alone, all the items together, or any combination or number of the items.

The terms "has," "contain(s)," and "include(s)" shall be interpreted to be synonymous with the term "comprise(s)" and as inclusive or open-ended such as to not exclude additional unrecited subject matter. Use of the four preceding terms also discloses and provides support for narrower alternative implementations, in which these terms are replaced by "consisting" or "consisting essentially of," which are closed as to exclude additional unrecited subject matter.

Unless otherwise indicated, all numbers or expressions, such as those expressing concentrations, ratios, counts, and the like, used in the specification (other than the claims) are understood to be modified in all instances by the term "approximately." At the very least, and not as an attempt to limit the application of the doctrine of equivalents to the claims, each numerical parameter recited in the specification or claims that is modified by the term "approximately" should be construed in light of the number of recited significant digits and by applying ordinary rounding techniques. All disclosed ranges are to be understood to encompass and provide support for claims that recite any subranges or any and all individual values subsumed by each range. For example, a stated range of "at least 90 percent" shall be construed as including support for at least 90 percent, at least 95 percent, at least 97 percent, at least 98 percent, at least 99 percent, at least 99.5 percent, at least 99.6 percent, at least 99.7 percent, at least 99.8 percent, and at least 99.9 percent.

The terms recited in the claims should be given their ordinary and customary meaning as determined by reference to relevant entries in widely used general dictionaries, relevant technical references, commonly understood meanings by those in the art, and the like with the understanding that the broadest meaning imparted by any one or combination of these sources should be given to the claim terms (for example, two or more relevant references should be combined to provide the broadest meaning of the combination of references) subject only to the following two exceptions: (a) when a term is used in a manner that is more expansive than its ordinary and customary meaning, then the term should be given its ordinary and customary meaning plus the additional expansive meaning, and (b) when a term has been explicitly defined to have a different meaning by reciting the term and its definition along with the phrase "in this disclosure" or similar language, then the term shall be limited to the definition. References to specific examples shall not invoke the foregoing exception (b) or otherwise restrict the scope of the recited claim terms. Other than situations where the foregoing exception (b) applies, nothing contained in this document should be considered a disclaimer or disavowal of claim scope.

The subject matter recited in the claims is not coextensive with and should not be interpreted to be coextensive with any implementation, feature, or combination of features described or illustrated in this document. This is true even if only a single implementation of the feature or combination of features is illustrated and described.

The entire content of each document listed below is incorporated by reference into this document (the documents below are collectively referred to as the "incorporated documents"). If the same term is used in both this document and one or more of the incorporated documents, then the term should be interpreted to have the broadest meaning imparted by any one or combination of these sources unless the term has been explicitly defined to have a different meaning in this document. If there is an inconsistency between any incorporated document and this document, then this document shall govern. The incorporated subject matter should not be used to limit or narrow the scope of the explicitly recited or depicted subject matter.

U.S. Pat. No. 5,731,168 A, entitled "Method for making heteromultimeric polypeptides," granted Mar. 24, 1998;

U.S. Pat. No. 5,877,296 A, entitled "Process for preparing conjugates of methyltrithio antitumor agents," granted Mar. 2, 1999;

U.S. Pat. No. 6,565,827 B1, entitled "Radioimmunotherapy of lymphoma using anti-CD20 antibodies," granted May 20, 2003;

U.S. Pat. No. 7,422,739 A, entitled "Anti-CD20 antibodies," granted Sep. 9, 2008;

U.S. Pat. No. 7,446,190 B2, entitled "Nucleic acids encoding chimeric T cell receptors," granted Nov. 4, 2008;

U.S. Pat. No. 7,741,465 B1, entitled "Chimeric receptor genes and cells transformed therewith," granted Jun. 22, 2010;

U.S. Pat. No. 8,088,387 B2, entitled "Method of targeting specific cell populations using cell-binding agent maytansinoid conjugates linked via a non-cleavable linker, said conjugates, and methods of making said conjugates," granted Jan. 3, 2012;

U.S. Pat. No. 8,277,806 B2, entitled "Use of trifunctional bispecific and trispecific antibodies for the treatment of malignant ascites," granted Oct. 2, 2012;

U.S. Pat. No. 8,592,562 B2, entitled "Method for making antibody Fc-heterodimeric molecules using electrostatic steering effects," granted Nov. 26, 2013;

U.S. Pat. No. 9,499,629 B2, entitled "Use of chimeric antigen receptor-modified T-cells to treat cancer," granted Nov. 22, 2016;

U.S. Pat. No. 9,505,848 B2, entitled "Engineered heterodimeric protein domains," granted Nov. 29, 2016;

U.S. Pat. No. 9,862,769 B2, entitled "Monoclonal antibodies against HER2," granted Jan. 9, 2018;

U.S. Pat. No. 10,011,858 B2, entitled "Methods for producing polypeptides by regulating polypeptide association," granted Jul. 3, 2018;

U.S. Pat. No. 10,322,192 B2, entitled "Eribulin-based antibody-drug conjugates and methods of use," granted Jun. 18, 2019;

U.S. Pat. No. 10,344,050 B2, entitled "Production of heterodimeric proteins," granted Jul. 9, 2019;

U.S. Pat. No. 10,517,960 B2, entitled "Bifunctional polypeptides," published Dec. 31, 2019;

U.S. Pat. No. 10,596,270 B2, entitled "Anti-folate receptor antibody conjugates, compositions comprising anti-folate receptor antibody conjugates, and methods of making and using anti-folate receptor antibody conjugates," granted Mar. 24, 2020;

U.S. Pat. No. 10,597,464 B2, entitled "Heterodimeric antibody Fc-containing proteins and methods for production thereof," granted Mar. 24, 2020;

U.S. Pat. No. 10,752,683 B2, entitled "Folate receptor 1 antibodies and immunoconjugates and uses thereof," granted Aug. 25, 2020;

U.S. Pat. No. 11,597,766 B2, entitled "Treatment of acute lymphoblastic leukemia," published Mar. 7, 2023;

U.S. Patent Application Publication No. 2023/0201210 A1, entitled "Combinations of anti-her2 antibody-drug conjugate and chemotherapeutic agents, and methods of use," published Jun. 29, 2023;

Kabat, E. A. et al., "Sequences of proteins of immunological interest." 5th Edition US Department of Health and Human Services, NIH publication No. 91-3242 (1991);

Shopes, B., "A genetically engineered human IgG mutant with enhanced cytolytic activity," THE JOURNAL OF IMMUNOLOGY, 1992 May 1; 148(9):2918-22;

Shopes, B., "A genetically engineered human IgG with limited flexibility fully initiates cytolysis via complement," MOLECULAR IMMUNOLOGY, 1993 April; 30(6):603-9; and van der Neut Kolfschoten, M. et al., "Anti-inflammatory activity of human IgG4 antibodies by dynamic Fab arm exchange," SCIENCE, 2007 September 14; 317(5844): 1554-7.

What is claimed is:

1. A method of treating cancer in a human subject, comprising:
    administering an immunotherapeutic agent to the human subject, wherein the immunotherapeutic agent comprises an antibody that binds human folate receptor alpha, wherein said antibody comprises:
    a first variable domain that further comprises a VH CDR1 region comprising SEQ ID NO: 5, a VH CDR2 region comprising SEQ ID NO: 6, and a VH CDR3 region comprising SEQ ID NO: 7; and
    a second variable domain that further comprises a VL CDR1 region comprising SEQ ID NO: 8, a VL CDR2 region comprising SEQ ID NO: 9, and a VL CDR3 region comprising SEQ ID NO: 10.

2. The method of claim 1, wherein:
    the first variable domain of the antibody comprises an amino acid sequence that has at least 90 percent sequence homology with SEQ ID NO: 3; and
    the second variable domain of the antibody comprises an amino acid sequence that has at least 90 percent sequence homology with SEQ ID NO: 4.

3. The method of claim 1, wherein the antibody is an IgG antibody.

4. The method of claim 1, wherein:
    the antibody comprises two heavy chains and two light chains;
    each of the two heavy chains has at least 90 percent sequence homology with SEQ ID NO: 11; and
    each of the two light chains has at least 90 percent sequence homology with SEQ ID NO: 12.

5. The method of claim 1, wherein the cancer is epithelial ovarian cancer.

6. The method of claim 1, comprising identifying that a tissue sample of the human subject comprises either RNA encoding folate receptor alpha or folate receptor alpha protein prior to the administering.

7. The method of claim 6, wherein the tissue sample is a blood sample.

8. The method of claim 6, wherein the tissue sample is a biopsy.

9. The method of claim 1, wherein the administering is selected from intravenous, intramuscular, subcutaneous, intradermal, intraocular, parenteral, intraperitoneal, intrathecal, intralesional, and intratumoral administering.

* * * * *